(12) United States Patent
Schleith et al.

(10) Patent No.: US 9,194,810 B2
(45) Date of Patent: Nov. 24, 2015

(54) METHOD AND DEVICE FOR THE DETECTION OF SURFACE DEFECTS OF A COMPONENT

(75) Inventors: Christian Schleith, Neubeuern (DE); Horst Winterberg, Bad Feilnbach (DE); Marcus Steinbichler, Neubeuern (DE)

(73) Assignee: Steinbichler Optotechnik GmbH, Neubeuern (DE)

( * ) Notice: Subject to any disclaimer, the term of this patent is extended or adjusted under 35 U.S.C. 154(b) by 1825 days.

(21) Appl. No.: 12/228,061

(22) Filed: Aug. 8, 2008

(65) Prior Publication Data
US 2009/0079972 A1 Mar. 26, 2009

(30) Foreign Application Priority Data
Aug. 10, 2007 (DE) .......................... 10 2007 037 812

(51) Int. Cl.
*G01N 21/00* (2006.01)
*G01N 21/88* (2006.01)

(52) U.S. Cl.
CPC .................................. *G01N 21/8806* (2013.01)

(58) Field of Classification Search
CPC .............................. G01N 21/00; G01N 33/00
USPC ........................................... 356/237.1–237.5
See application file for complete search history.

(56) References Cited

U.S. PATENT DOCUMENTS

| | | | | |
|---|---|---|---|---|
| 5,056,922 A | * | 10/1991 | Cielo et al. | 356/604 |
| 5,598,262 A | * | 1/1997 | Jutard et al. | 356/239.1 |
| 5,963,328 A | * | 10/1999 | Yoshida et al. | 356/600 |
| 7,453,563 B2 | * | 11/2008 | Rudert et al. | 356/239.1 |
| 2004/0233421 A1 | * | 11/2004 | Weinhold | 356/237.1 |
| 2007/0263206 A1 | * | 11/2007 | LeBlanc et al. | 356/239.7 |

FOREIGN PATENT DOCUMENTS

| | | |
|---|---|---|
| DE | 10 2004 026 375 | 5/2004 |
| DE | 10 2004 058 778 | 8/2005 |
| DE | 20 2005 011 807 | 12/2005 |
| DE | 10 2005 031 490 | 2/2007 |
| JP | S57-178134 | 11/1982 |
| JP | H11-337502 | 12/1999 |
| JP | 2005-214978 | 8/2005 |

OTHER PUBLICATIONS

Office Action from Japanese Patent Office dated Sep. 18, 2012.

* cited by examiner

*Primary Examiner* — Tarifur Chowdhury
*Assistant Examiner* — Isiaka Akanbi
(74) *Attorney, Agent, or Firm* — Dilworth & Barrese, LLP

(57) ABSTRACT

A method serves the detection of surface defects of a component. The surface of the component (5) is radiated from the side with light from a light source (4, 4'). The light radiated back from the surface of the component (5) is detected by a sensor. To improve such a method, only a rear region (19, 19') of the surface of the component (5) is radiated with light from the light source (4, 4') and/or only the light radiated back from a rear region (19, 19') of the surface of the component (5) is detected by the sensor and/or evaluated by an evaluation device FIG. 3).

20 Claims, 2 Drawing Sheets

METHOD AND DEVICE FOR THE DETECTION OF SURFACE DEFECTS OF A COMPONENT

BACKGROUND OF THE INVENTION

The invention relates to a method for the detection of surface defects of a component or of any other object and to a device for the carrying out of such a method.

Various methods are already known for the detection of surface errors of components. In so-called dark field lighting, the surface of the component is radiated with light from a light source from the side. The light radiated back by the surface of the component is detected by a sensor or a camera, by a CCD camera for example. The image detected by the sensor can be evaluated and/or stored. Dark field lighting is in particular used for the detection of scratches or similar surface defects. In this respect, the surface of the component is illuminated such that light only enters into the optical sensor from the site of the defect, that is, of the scratch.

To illustrate the known method of dark field lighting

FIG. 1 shows a device for the detection of surface defects of a component in a schematic side view; and FIG. 2 shows a modified device in accordance with FIG. 1.

The device in accordance with FIG. 1 includes two light sources 4, 4' for the radiation of the surface of a component 5 from a respective side direction and a CCD camera 2 having a sensor for the detection of the light radiated back from the surface of the component 5. The light sources 4, 4' are disposed opposite one another. They are arranged symmetrically to the center axis of the CCD camera 2. Directed light from the light sources 4, 4' is incident onto the surface of the component 5.

The measured zone A is determined by the aperture 6 of the CCD camera 2 and the spacing of the CCD camera 2 from the component 5. The light sources 4, 4' are arranged such that no light enters into the CCD camera 2 by the reflection on the surface of the component 5. The light source 4 radiates directed light from the left hand side onto the measured zone A at an opening angle α. The lower boundary ray 7 is incident to the surface of the component 5 at an angle β in the left hand end point 8 of the measured zone A and is reflected from there as a beam 9. The arrangement is made such that the reflected beam 9 is not incident into the CCD camera 2, but is radiated below the CCD camera 2.

The upper boundary ray 10 from the light source 4 leads to the right hand end 8' of the measured zone A and is reflected from there at an angle γ which is smaller than the angle β which is likewise not incident into the CCD camera 2, but is radiated below the CCD camera 2.

The light source 4' is disposed on the oppositely disposed side of the measured zone A. The light radiated from this light source 4' onto the measured zone A is also not incident into the CCD camera 2 on the reflection on the surface of the component 5.

The methods and devices in accordance with FIG. 1 are known from various pre-publications, for example from DE 20 2005 011 807 U1, DE 10 2004 026 375 A1, DE 10 2004 058 778 A1 and DE 10 2005 031 490 A1.

In dark field lighting in accordance with FIG. 1, the light radiated from the light sources 4, 4' is radiated past the optical sensor in the CCD camera 2 in the manner visible from FIG. 1 with a defect-free surface of the component 5. From the view of the CCD camera 2, the measured zone A appears dark with a defect-free surface of the component 5.

If there is a scratch or a similar defect on the surface of the component 5, the light radiated from the light sources 4 and/or 4' is radiated back into the CC camera 2. Scratches on the surface of the component 5 can be recognized in this manner.

The sensitivity of the measurement is the larger, the smaller the angles β and γ are at which the rays 7, 10 or 7', 10' and the rays between them are incident onto the measured zone A. It is, however, frequently necessary for mechanical reasons that the light sources 4, 4' have to observe a specific minimum spacing from the surface of the component 5. The angles β und γ and the angles disposed therebetween are hereby increased.

An example for this is shown in FIG. 2. The angles β and γ increase due to the increase in the spacing of the light sources 4, 4' from the surface of the component 5. The reflected rays 9, 9' of the lower boundary rays 7, 7' enter into the CCD camera 2 and onto its sensor.

To prevent this and to be able to increase the sensitivity, the angles β and γ can be reduced in that the side spacing of the light sources 4, 4' from the measured zone A is increased. However, the total arrangement or the device in which the light sources 4, 4' are located is hereby also increased. Since a specific spacing of the light sources 4 from the surface of the component 5 has to be observed, either the sensitivity therefore decreases or the construction size of the device or of the inspection arrangement increases.

SUMMARY OF THE INVENTION

It is the object of the invention to improve a method and a device of the initially named kind.

In accordance with a first proposal, this object is solved in a method for the detection of surface defects of a component in accordance with the characterizing features herein. Only a rear region of the surface of the component is radiated with light from the light source and/or only the light radiated back from a rear region of the surface of the component is detected by the sensor and/or evaluated by an evaluation device. Since only one region of the surface of the component at the rear—viewed from the light source—is radiated with light from the light source, the angle of incidence of the lower boundary ray becomes smaller with respect to the surface of the component so that the sensitivity can be increased. Alternatively, with unchanging sensitivity, the side spacing of the light source from the component can be increased.

Advantageous further developments are described herein.

The surface of the component can be radiated with light from a plurality of light sources. The surface of the component can in particular be radiated with light from two light sources. The two light sources are preferably disposed opposite one another. It is, however, also possible to use a plurality of light sources which are arranged in ring shape around the component. Bar-shaped light sources or light sources having any other elongate extent are particularly suitable.

In a device for the detection of surface defects of a component in accordance with the description herein, the object underlying the invention is solved in accordance with a first proposal by the characterizing features herein.

Advantageous further developments are described herein.

In a method for the detection of surface defects of a component in accordance with the description herein, the object underlying the invention is solved in accordance with a further proposal for which protection is claimed independently by the characterizing features herein. In accordance with this proposal, the surface of the component is radiated from the side with light from a strip projector. The light radiated back from the surface of the component is detected by the sensor. Areal deformations of the surface of the component such as in particular dents or dimples can be recognized by the deformation of the strips on this surface. Furthermore, surface defects such as in particular scratches can also be recognized by the radiation of the surface of the component from the side with light from a light source, that is, by this dark field lighting.

The two methods in accordance with the invention can be combined with one another.

The object underlying the invention is solved in a device for the detection of surface defects of a component in accordance with a further proposal. The device includes a strip projector for the projection of a strip pattern onto the surface of the component from a side direction.

The two devices in accordance with the invention can be combined with one another.

BRIEF DESCRIPTION OF THE DRAWINGS

Embodiments of the invention will be explained in detail in the following with reference to the enclosed drawing. There are shown in the drawing

DESCRIPTION OF THE PREFERRED EMBODIMENTS

Figure 1:
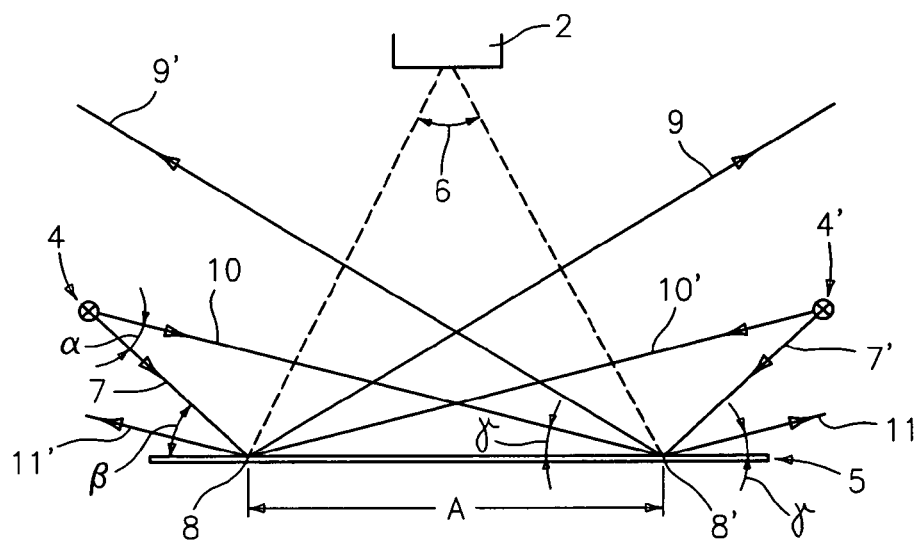
FIG. 1 shows a device for the detection of surface defects of a component in a schematic side view.
Figure 2:
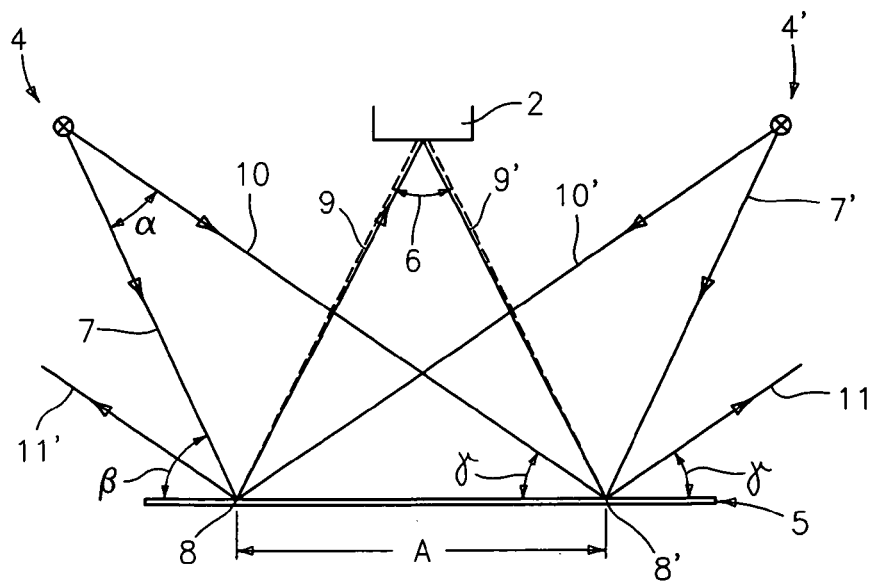
FIG. 2 shows a modified device in accordance with FIG. 1.
Figure 3:
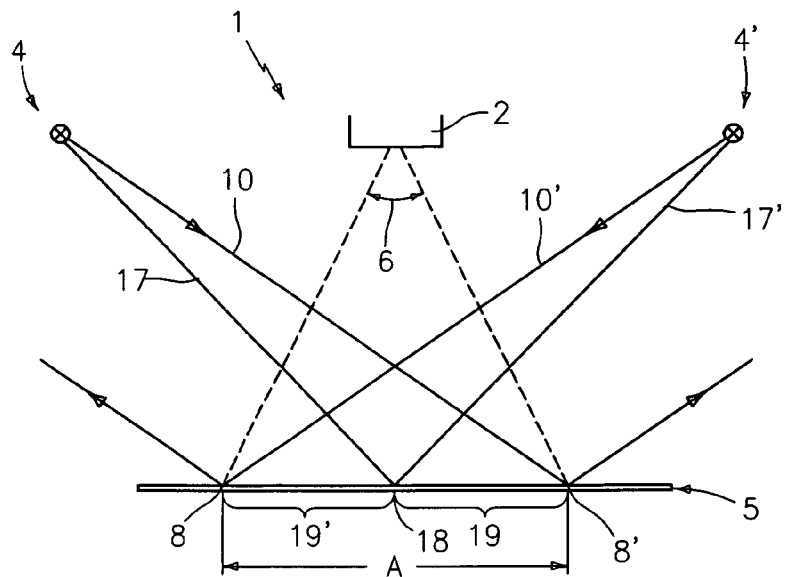
FIG. 3 an embodiment of a device in accordance with the invention for the detection of surface defects of a component in a schematic side view.

In the embodiment shown in FIG. 3, components which correspond to those of FIGS. 1 and 2 are provided with the same reference numerals so that they do not have to be described again.

The cone of light from the light source 4 is set such that the lower-boundary ray 17 is incident onto the surface of the component 5 at the point 18 at the center of the measured zone A. The same applies to the lower boundary ray 17' from the oppositely disposed light source 4'. The upper boundary rays 10, 10' of the light sources 4, 4' are, as also in the previously known embodiments in accordance with FIGS. 1 and 2, incident on the respective rear end points 8', 8 on the surface of the component 5. Viewed from the light source, only the rear region 19 of the surface of the component 5 is radiated with light from the light source 4 in this manner. In a corresponding manner, only the rear region 19' of the surface of the component 5 is radiated with light from the light source 4'.

In the embodiment in accordance with FIG. 3, the surface of the component 5 or the measured zone A is radiated with light from two mutually oppositely disposed light sources 4, 4'. It would, however, also be possible to arrange a plurality of light sources in ring shape around the component 5 or the measured zone A (not shown in the drawing). The light sources 4, 4' can be substantially in dot shape. It is, however, also possible to use bar-shaped light sources, with the direction of the elongate extent preferably being disposed perpendicular to the plane of the drawing of FIG. 3.

It is furthermore possible to use the arrangement in accordance with FIG. 2 for the realization of the invention and only to detect the light radiated back from the respective rear region of the surface of the component 5 by the sensor in the CCD camera 2 and/or to evaluate it by an evaluation device. For this purpose, the method can be carried out in a manner such that in each case only one of the light sources 4, 4' lights up. If, for example, the light source 4 is switched on, the left hand region of the lens of the CCD camera 2 can be covered by a cap (now shown in the drawing) so that only the light radiate back by the rear region 19 of the surface of the component 5 is detected by the sensor in the CCD camera. For the inspection of the left hand region 19' of the measured zone A, the light source 4 can be switched off and the light source 4' can be switched on and a cap covers the right hand part of the lens of the CCD camera 2. In this second part of the measurement, only the light radiated back from the rear region 19' of the surface of the component 5 is then detected by the sensor in the CCD camera 2.

The following method can furthermore be carried out: The light source 4 is first switched on which illuminates the total measured zone A as shown in FIG. 2. However, only the light radiated back from the rear region 19 of the surface of the component 5 is evaluated. In a second step, the light source 4 is switched off and the light source 4' is switched on and only the light radiated back from the rear region 19' is evaluated.

Figure 4A:
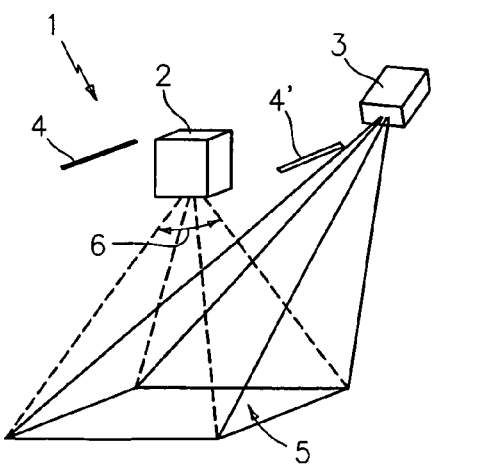
FIG. 4 a further embodiment of a device in accordance with the invention with a strip projector.
Figure 4B:
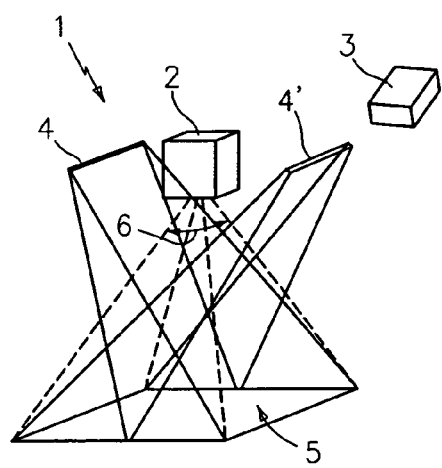

In the embodiment in accordance with FIG. 4, a strip projector 3 is present in addition to the bar-shaped light source 4, 4'. The strip projector 3 is disposed approximately at the same level as the light sources 4, 4' and the CCD camera 2. It is, however, disposed between the light sources 4, 4' and the spacing from the CCD camera 2. Viewed in the peripheral direction, the strip projector 3 is offset by 90° in each case with respect to the light sources 4, 4'. Directed light is cast by the strip projector 3 onto the surface of the component 5 at a specific angle, namely the triangulation angle. The strip projector 3 projects a strip patter onto the surface of the component 5.

On the operation of the device in accordance with FIG. 3, the light sources 4, 4' can be switched off and the strip projector 3 can be switched on, as shown in FIG. 4a. The strips projected onto the surface of the component 5 by the strip projector 3 are deformed by areal deformations of this surface such as dents or dimples. These areal deformations can be detected by the CCD camera 2 and evaluated due to the deformation of the strips.

It is furthermore possible to switch off the strip projector 3 and to switch on the light sources 4, 4', with these light sources 4, 4' being able to light up simultaneously or to be able to be switched on alternately. The light sources 4, 4' generate dark field lighting by which it is possible to recognize sharp-edged defect sites such as in particular scratches. The improved method in accordance with FIG. 3 can be carried out with the dark field lighting with the light sources 4, 4'. It is, however, also possible to use conventional methods in accordance with FIGS. 1 and 2.

The construction size of the inspection device can be minimized by the invention without increasing the angle of incidence of the light rays from the light sources 4, 4' and thus losing sensitivity. This angle substantially describes the sensitivity of the measurement. If a specific spacing of the light sources 4, 4' from the surface of the component 5 has to be observed for mechanical reasons, the spacing of a light source 4, 4' from the center axis of the CCD camera 2 or the spacing of the light sources 4, 4' from one another and thus the construction size of the inspection unit are preset with a demanded measuring sensitivity and thus a demanded maximum angle of incidence. To minimize the construction size of the inspection unit without increasing the angle of incidence of the radiation and thus without losing sensitivity, the light sources 4, 4' do not each illuminate the total measured zone A together, but rather in each case only the rear part or the oppositely disposed part. The spacing between the light sources 4, 4' can be reduced in this manner without the angle of incidence of the radiation on the surface of the component 5 and thus the measurement sensitivity changing.

The invention can be realized in a manner such that the light sources 4, 4' only illuminate the respective oppositely disposed side of the measured zone A so that with a component free of defects the light is largely reflected past the sensor of the CCD camera. An illumination from more than two sides, up to an annular illumination, is also possible. It is likewise possible to illuminate the respective total image field sequentially by the light sources and only to take the respective oppositely disposed image half into account in the image evaluation.

With a strip projector, light directed from the strip projector 3 is as a rule incident onto the component to be inspected at a specific angle (triangulation angle). Areal deformations of the surface such as dents and dimples can be recognized by the deformation of the strips. The detection of sharp-edged defect sites such as scratches is, however, only possible with reservations with a strip projector since the light only comes from one direction from the strip projector. Accordingly, an additional shot it taken using a lighting device perpendicular to the strip projection from the light sources 4, 4'. To keep the construction size of the device as compact as possible, the method in accordance with FIG. 3 can be carried out in which in each case only the rear region of the measured zone is radiated.

The invention claimed is:

1. A method for the detection of surface defects of a component (5),
    wherein the surface of the component (5) is radiated from the side with light from a light source (4, 4');
    the light radiated back from the surface of the component (5) is detected by a sensor;
    only a rear region (19, 19') of the surface of the component (5) is radiated with light from the light source (4, 4');
    and/or in that only the light radiated back from a rear region (19, 19') of the surface of the component (5) is detected by the sensor and/or is evaluated by an evaluation device,
    wherein the light source and the sensor are arranged such that in the absence of surface defects no light enters into the sensor by the reflection on the surface of the component.

2. A method in accordance with claim 1, wherein the surface of the component (5) is radiated with light from a plurality of light sources (4, 4').

3. A method in accordance with claim 2, wherein the surface of the component (5) is radiated with light from two light sources (4, 4') disposed mutually opposite.

4. A method in accordance with claim 3, wherein the surface of the component (5) is radiated with light from a bar-shaped light source (4, 4').

5. A method in accordance with claim 2, wherein the surface of the component (5) is radiated with light from a plurality of light sources arranged around the component (5) in ring shape.

6. A method in accordance with claim 5, wherein the surface of the component (5) is radiated with light from a bar-shaped light source (4, 4').

7. A method in accordance with claim 2, wherein the surface of the component (5) is radiated with light from a bar-shaped light source (4, 4').

8. A method in accordance with claim 1, wherein the surface of the component (5) is radiated with light from a bar-shaped light source (4, 4').

9. A device for the detection of surface defects of a component
    comprising a light source (4, 4') for the radiation of the surface of the component (5) from a side direction;
    and comprising a sensor for the detection of the light radiated back from the surface of the component (5), wherein
    only a rear region (19, 19') of the surface of the component (5) is radiated with light from the light source (4, 4');
    and/or in that only the light radiated back from a rear region (19, 19') of the surface of the component (5) is detected by the sensor and/or is evaluated by an evaluation device,
    wherein the light source and the sensor are arranged such that in the absence of surface defects no light enters into the sensor by the reflection on the surface of the component.

10. A device in accordance with claim 9, comprising a plurality of light sources (4, 4') for the radiation of the surface of the component (5).

11. A device in accordance with claim 10, comprising two oppositely disposed light sources (4, 4') for the radiation of the surface of the component (5).

12. A device in accordance with claim 10, comprising a plurality of light sources arranged around the component in ring shape for the radiation of the surface of the component (5).

13. A device in accordance with claim 10, wherein the light sources (4, 4') are bar-shaped.

14. A device in accordance with claim 9, wherein the light sources (4, 4') are bar-shaped.

15. A method for the detection of surface defects of a component (5),
    wherein the surface of the component (5) is radiated from the side with light from a light source (4, 4');
    the light radiated back from the surface of the component (5) is detected by a sensor;
    only a rear region (19, 19') of the surface of the component (5) is radiated with light from the light source (4, 4'); and
    the surface of the component (5) is radiated from the side with light from a strip projector (3),
    wherein the light source and the sensor are arranged such that in the absence of surface defects no light enters into the sensor by the reflection on the surface of the component.

16. A method in accordance with claim 15, wherein only a rear region (19, 19') of the surface of the component (5) is radiated with light from the light source (4, 4') and/or only the light radiated back from a rear region (19, 19') of the surface of the component (5) is detected by the sensor and/or is evaluated by an evaluation device.

17. A method in accordance with claim 15, wherein the surface of the component (5) is radiated with light from a plurality of light sources (4, 4').

18. A device for the detection of surface defects of a component (5)
    comprising a light source (4, 4') for the radiation of the surface of the component (5) from a side direction;
    a sensor for the detection of the light radiated back from the surface of the component (5),
    only a rear region (19, 19') of the surface of the component (5) is radiated with light from the light source (4, 4'), and
    a strip projector (3) for the projection of a strip pattern from a side direction onto the surface of the component (5), wherein the light source and the sensor are arranged such that in the absence of surface defects no light enters into the sensor by the reflection on the surface of the component.

19. A device in accordance with claim 18, wherein only a rear region (19, 19') of the surface of the component (5) is radiated with light from the light source (4, 4'); and/or only the light radiated back from a rear region (19, 19') of the surface of the component (5) is detected by the sensor and/or is evaluated by an evaluation device.

20. A device in accordance with claim 18, wherein only a rear region (19, 19') of the surface of the component (5) is radiated with light from the light source (4. 4');

and/or in that only the light radiated back from a rear region (19, 19') of the surface of the component (5) is detected by the sensor and/or is evaluated by an evaluation device.

\* \* \* \* \*